United States Patent
He et al.

(10) Patent No.: US 12,290,399 B2
(45) Date of Patent: May 6, 2025

(54) METHOD, APPARATUS AND DEVICE FOR MEASURING THICKNESS OF SUBCUTANEOUS TISSUE, AND STORAGE MEDIUM

(71) Applicant: WUXI HISKY MEDICAL TECHNOLOGIES CO., LTD., Jiangsu (CN)

(72) Inventors: Qiong He, Jiangsu (CN); Jinhua Shao, Jiangsu (CN); Jin Sun, Jiangsu (CN); Houli Duan, Jiangsu (CN)

(73) Assignee: WUXI HISKY MEDICAL TECHNOLOGIES CO., LTD., Jiangsu (CN)

( * ) Notice: Subject to any disclaimer, the term of this patent is extended or adjusted under 35 U.S.C. 154(b) by 653 days.

(21) Appl. No.: 17/631,103

(22) PCT Filed: Jul. 28, 2020

(86) PCT No.: PCT/CN2020/105022
§ 371 (c)(1),
(2) Date: Jan. 28, 2022

(87) PCT Pub. No.: WO2021/018108
PCT Pub. Date: Feb. 4, 2021

(65) Prior Publication Data
US 2022/0273259 A1    Sep. 1, 2022

(30) Foreign Application Priority Data
Aug. 1, 2019   (CN) .......................... 201910706602.1

(51) Int. Cl.
*A61B 8/08*   (2006.01)
*A61B 8/00*   (2006.01)

(52) U.S. Cl.
CPC .......... *A61B 8/0858* (2013.01); *A61B 8/4245* (2013.01); *A61B 8/5223* (2013.01); *A61B 8/5269* (2013.01)

(58) Field of Classification Search
CPC ... A61B 8/0858; A61B 8/4245; A61B 8/5223; A61B 8/5269
See application file for complete search history.

(56) References Cited

U.S. PATENT DOCUMENTS

| | | | | |
|---|---|---|---|---|
| 5,615,681 A | * | 4/1997 | Ohtomo | G01N 29/07 600/459 |
| 2007/0016050 A1 | * | 1/2007 | Moehring | A61B 8/488 600/454 |

(Continued)

FOREIGN PATENT DOCUMENTS

| | | |
|---|---|---|
| CN | 101527047 A | 9/2009 |
| CN | 102636252 A | 8/2012 |

(Continued)

OTHER PUBLICATIONS

Zhang, X., et al. "Study on Precision Measurement of Ultrasonic Wave Transmission Time and Its Applications." Journal of Beijing Institute of Technology, Jun. 2011, 31(6): Abstract.

*Primary Examiner* — Sean A Frith
(74) *Attorney, Agent, or Firm* — SALIWANCHIK, LLOYD & EISENSCHENK (57) ABSTRACT

Provided are method, apparatus and device for measuring a thickness of a subcutaneous tissue, and a computer-readable storage medium. The method includes: emitting ultrasonic detection waves inwards from a skin surface, and acquiring ultrasonic echo signals of the ultrasonic detection waves; determining, according to ultrasonic parameter values of the ultrasonic echo signals and a characteristic parameter threshold of a subcutaneous tissue, the moment the ultrasonic echo signals from the boundary of the subcutaneous tissue are (Continued)

received; and calculating a thickness of the subcutaneous tissue according to the moment the ultrasonic echo signals from the boundary of the subcutaneous tissue are received, thereby enabling a precise measure of the thickness of the subcutaneous tissue.

13 Claims, 3 Drawing Sheets

(56) References Cited

U.S. PATENT DOCUMENTS

| | | | |
|---|---|---|---|
| 2017/0196536 A1* | 7/2017 | Govari | A61B 8/5207 |
| 2019/0336098 A1* | 11/2019 | Xu | A61B 8/5207 |
| 2021/0196227 A1* | 7/2021 | Salinas | A61B 8/465 |

FOREIGN PATENT DOCUMENTS

| | | |
|---|---|---|
| CN | 103096811 A | 5/2013 |
| CN | 103429163 A | 12/2013 |
| CN | 106137251 A | 11/2016 |
| CN | 106937864 A | 7/2017 |
| CN | 110313938 A | 10/2019 |
| JP | H10165401 A | 6/1998 |

\* cited by examiner

METHOD, APPARATUS AND DEVICE FOR MEASURING THICKNESS OF SUBCUTANEOUS TISSUE, AND STORAGE MEDIUM

CROSS REFERENCE TO RELATED APPLICATIONS

This application is a National Stage of International Application No. PCT/CN2020/105022, filed on Jul. 28, 2020, which claims priority to Chinese Patent Application No. 201910706602.1, filed on Aug. 1, 2019; both of which are hereby incorporated by reference in their entireties.

TECHNICAL FIELD

The present invention relates to the technical field of measurement of thickness of subcutaneous tissues, in particular to a method, apparatus and device for measuring a thickness of a subcutaneous tissue and a storage medium.

BACKGROUND

Drug administration to patients includes oral administration and injection. Drug administration is determined in consideration of the purpose of the drug administration, patient health factors, and the like. In the case of injection, a region of the body where injection is to be performed may be determined based on the purpose of drug administration, patient health factors, and the like.

Diabetic patients require periodic insulin administration, which is performed by injection. Insulin is most often injected subcutaneously, and is primarily injected into the abdomen, the arms, the thighs, the buttocks, and other parts of the body.

Subcutaneous tissues, often referred to as superficial fascia, are loose connective tissue and adipose tissue beneath the skin which connect the skin to the muscles. Since the subcutaneous tissues are located between the skin and the muscles, a too short injection needle may cause insulin to be administered to the skin, while a too long injection needle may cause insulin to be administered to the muscles. Therefore, although it may be necessary to select an appropriate injection needle length in accordance with the thickness of the subcutaneous tissues, the impossibility of observing the thickness of the subcutaneous tissues prohibits safe and effective insulin supply. How to accurately measure the thickness of the subcutaneous tissues has become an urgent technical problem to be solved.

SUMMARY

The present invention provides a method, apparatus and device for measuring a thickness of a subcutaneous tissue and a storage medium, which are used for accurately measuring the thickness of the subcutaneous tissues.

One aspect of the present invention provides a method for measuring a thickness of a subcutaneous tissue, including:
emitting ultrasonic detection waves inwards from a skin surface, and acquiring ultrasonic echo signals of the ultrasonic detection waves;
determining, according to ultrasonic parameter values of the ultrasonic echo signals and a characteristic parameter threshold of a subcutaneous tissue, the moment the ultrasonic echo signals from the boundary of the subcutaneous tissue are received; and
calculating a thickness of the subcutaneous tissue according to the moment the ultrasonic echo signals from the boundary of the subcutaneous tissue are received.

Another aspect of the present invention provides an apparatus for measuring a thickness of a subcutaneous tissue, including:
a measuring module, configured for emitting ultrasonic detection waves inwards from a skin surface and acquiring ultrasonic echo signals of the ultrasonic detection waves;
a boundary determination module, configured for determining, according to ultrasonic parameter values of the ultrasonic echo signals and a characteristic parameter threshold of a subcutaneous tissue, the moment the ultrasonic echo signals from the boundary of the subcutaneous tissue are received; and
a thickness calculation module, configured for calculating a thickness of the subcutaneous tissue according to the moment the ultrasonic echo signals from the boundary of the subcutaneous tissue are received.

Another aspect of the present invention provides a device for measuring a thickness of a subcutaneous tissue, including:
a memory, a processor, and a computer program stored in the memory and executable by the processor, wherein the processor implements the aforementioned method for measuring a thickness of a subcutaneous tissue when running the computer program.

Another aspect of the present invention provides a computer-readable storage medium having a computer program stored therein, wherein
the computer program implements the aforementioned method for measuring a thickness of a subcutaneous tissue when executed by a processor.

According to the method, apparatus and device for measuring a thickness of a subcutaneous tissue and the storage medium provided by the present invention, ultrasonic detection waves are emitted inwards from a skin surface by an ultrasonic detector, and ultrasonic echo signals of the ultrasonic detection waves are received; the moment the ultrasonic echo signals from the boundary of a subcutaneous tissue are received is determined according to ultrasonic parameter values of the ultrasonic echo signals and a characteristic parameter threshold of the subcutaneous tissue; a thickness of the subcutaneous tissue is calculated according to the moment the ultrasonic echo signals from the boundary of the subcutaneous tissue are received, thereby providing a precise measurement of the thickness of the subcutaneous tissue.

Through the above drawings, specific embodiments of the present invention have been shown, which will be described in more detail hereinafter. The drawings and written description are not intended to limit the scope of the inventive concept in any way, but rather to illustrate the inventive concept to those skilled in the art by reference to specific embodiments.

DETAILED DESCRIPTION

The exemplary embodiments will now be described in detail, and examples thereof are illustrated in the drawings. When reference to the drawings is made in the following description, identical numerals in the different drawings represent the same or similar elements, unless otherwise indicated. The implementations described in the following exemplary embodiments do not represent all implementations consistent with the present invention. Rather, they are merely examples of an apparatus and a method consistent with certain aspects of the present invention, as detailed in the appended claims.

The terms "first", "second", etc. referred to herein are used for descriptive purposes only and are not to be construed as indicating or implying relative importance or implicitly indicating the number of technical features indicated. In the description of the following embodiments, "a plurality of" means two or more, unless otherwise specifically defined.

These several specific embodiments below may be combined with one another, and the same or similar concepts or processes may not be repeated in some embodiments. The embodiments of the present invention will be described below with reference to the drawings.

Embodiment 1

Figure 1:
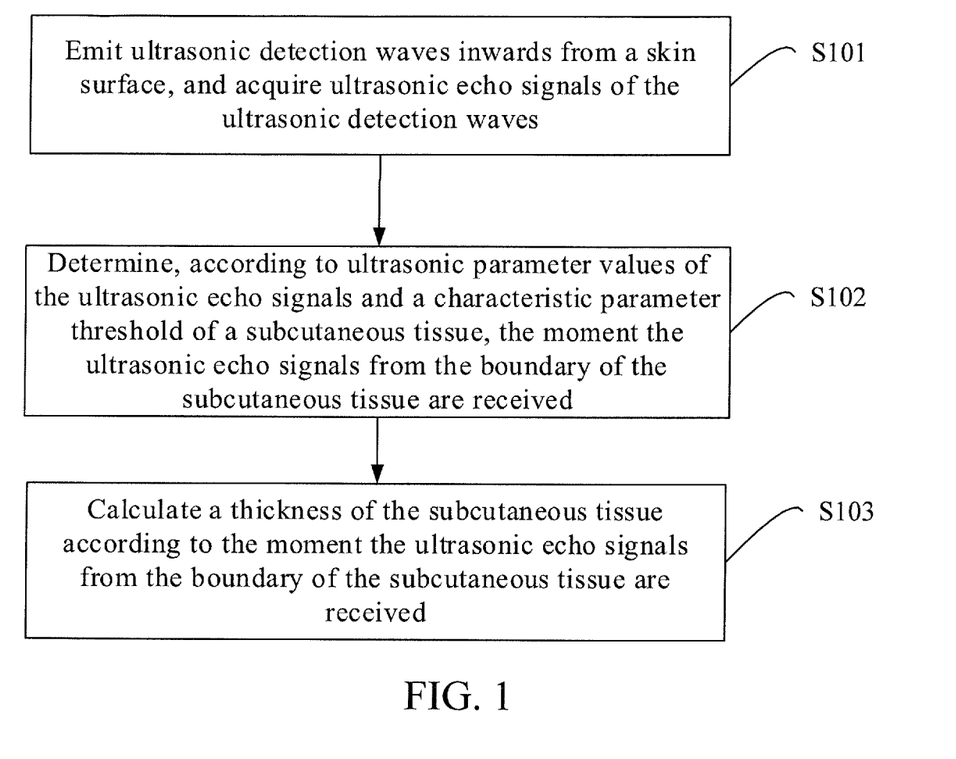
FIG. 1 is a flowchart of a method for measuring a thickness of a subcutaneous tissue according to Embodiment 1 of the present invention.

FIG. 1 is a flowchart of a method for measuring a thickness of a subcutaneous tissue according to Embodiment 1 of the present invention. As shown in FIG. 1, the method includes the following specific steps:

S101: emitting ultrasonic detection waves inwards from a skin surface, and acquiring ultrasonic echo signals of the ultrasonic detection waves;

An ultrasonic detector is used for emitting ultrasonic detection waves to a detected object and receiving ultrasonic echo signals generated by the ultrasonic detection waves passing through a subcutaneous tissue and a deep fascia layer.

In this embodiment, the moment the ultrasonic detector emits the ultrasonic detection waves and the received ultrasonic echo signals generated by the ultrasonic detection waves passing through the subcutaneous tissue and the deep fascia layer can be acquired.

S102: determining, according to ultrasonic parameter values of the ultrasonic echo signals and a characteristic parameter threshold of the subcutaneous tissue, the moment the ultrasonic echo signals from the boundary of the subcutaneous tissue are received;

The ultrasonic parameter includes at least one of: scattering peak, scatterer density, scatterer distribution characteristic, reflectance value, reflectance value distribution, etc. In addition, the ultrasonic parameter may also be other parameters that can reflect different reflection or transmission characteristics of the subcutaneous tissue and the deep fascia layer to the ultrasonic detection waves, which is not specifically limited by this embodiment here.

In this embodiment, the characteristic parameter threshold of the subcutaneous tissue is used to indicate the reflection or transmission characteristic of the subcutaneous tissue, and may be set by a skilled person according to a large number of experimental results and experiences, which is not specifically limited by this embodiment here.

Since the subcutaneous tissue and the deep fascia layer have the different reflection or transmission characteristics to the ultrasonic detection waves, the ultrasonic echo signals meeting the characteristic parameter threshold of the subcutaneous tissue and the ultrasonic echo signals not meeting the characteristic parameter threshold of the subcutaneous tissue may be separated according to the ultrasonic parameter values of the ultrasonic echo signals of the ultrasonic detection waves, so that the ultrasonic echo signals of the subcutaneous tissue can be obtained and the moment the ultrasonic echo signals from the boundary of the subcutaneous tissue are received can be further determined. The distance from the surface of the ultrasonic detector to the boundary of the subcutaneous tissue is the thickness of the subcutaneous tissue.

S103: calculating a thickness of the subcutaneous tissue according to the moment the ultrasonic echo signals from the boundary of the subcutaneous tissue are received.

According to the moment the ultrasonic echo signals from the boundary of the subcutaneous tissue are received and the moment the ultrasonic detector emits the ultrasonic detection waves, a time interval from the emission of the ultrasonic detection waves to the reception of the ultrasonic echo signals from the boundary of the subcutaneous tissue can be calculated, and according to the time interval and the speed of the ultrasonic echo signals propagating in the subcutaneous tissue, a thickness value of the subcutaneous tissue can be calculated.

According to the embodiment of the present invention, ultrasonic detection waves are emitted inwards from a skin surface by an ultrasonic detector, and ultrasonic echo signals of the ultrasonic detection waves are received; the moment the ultrasonic echo signals from the boundary of a subcutaneous tissue are received is determined according to ultrasonic parameter values of the ultrasonic echo signals and a characteristic parameter threshold of the subcutaneous tissue; a thickness of the subcutaneous tissue is calculated according to the moment the ultrasonic echo signals from the boundary of the subcutaneous tissue are received, and thereby the thickness of the subcutaneous tissue can be accurately measured.

Embodiment 2

Figure 2:
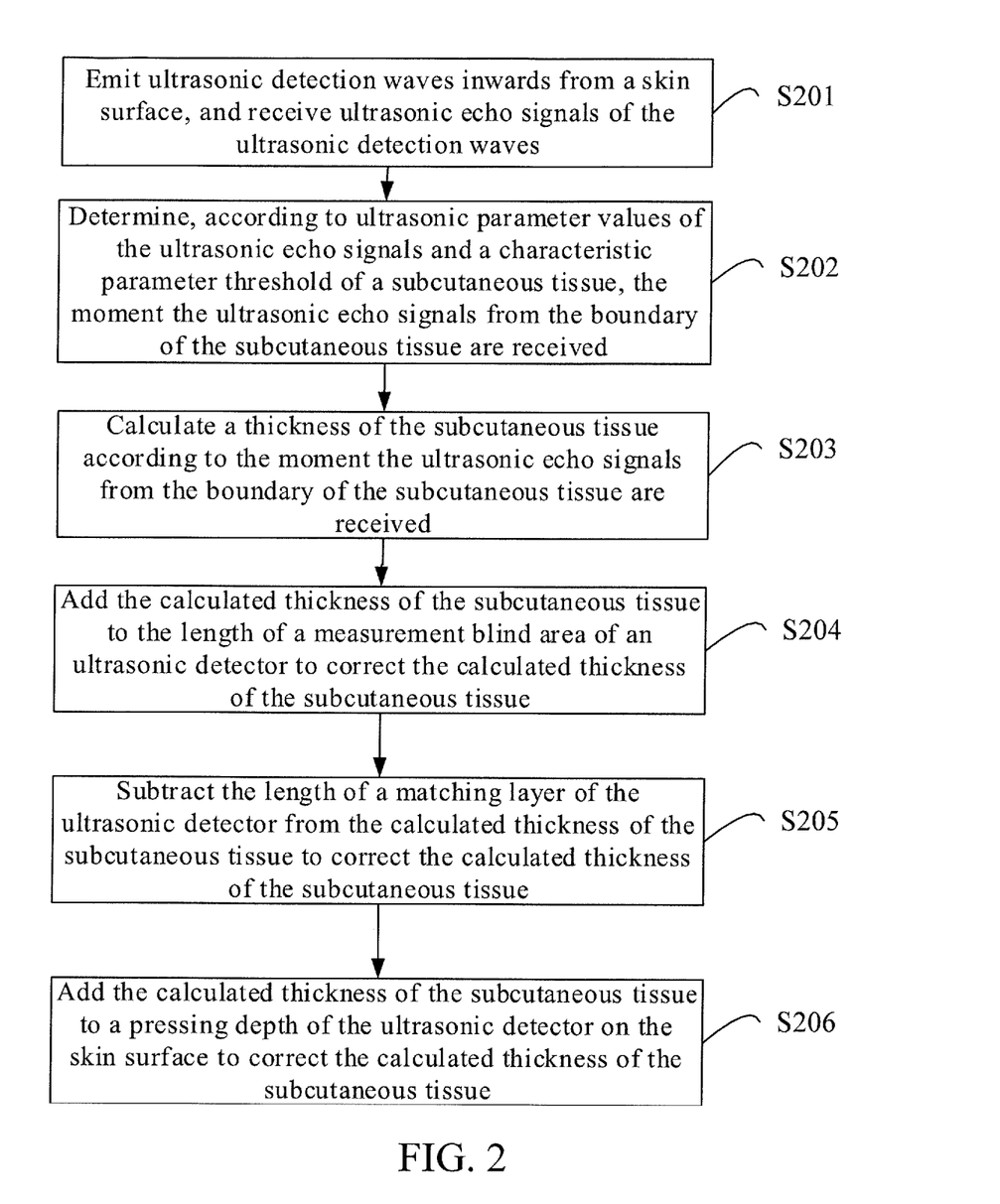
FIG. 2 is a flowchart of a method for measuring a thickness of a subcutaneous tissue according to Embodiment 2 of the present invention.

FIG. 2 is a flowchart of a method for measuring a thickness of a subcutaneous tissue according to Embodiment 2 of the present invention. On the basis of Embodiment 1 described above, in this embodiment, after the calculating a thickness of the subcutaneous tissue according to the moment the ultrasonic echo signals from the boundary of the subcutaneous tissue are received, the method further includes correcting the calculated thickness of the subcutaneous tissue. As shown in FIG. 2, the method includes the following specific steps:

S201: emitting ultrasonic detection waves inwards from a skin surface, and receiving ultrasonic echo signals of the ultrasonic detection waves;

An ultrasonic detector is used for emitting ultrasonic detection waves to a detected object and receiving ultrasonic echo signals generated by the ultrasonic detection waves passing through a subcutaneous tissue and a deep fascia layer.

S202: determining, according to ultrasonic parameter values of the ultrasonic echo signals and a characteristic parameter threshold of the subcutaneous tissue, the moment the ultrasonic echo signals from the boundary of the subcutaneous tissue are received;

The ultrasonic parameter is any of: scattering peak, scatterer density, scatterer distribution characteristic, reflectance value, reflectance value distribution, etc. In addition, the ultrasonic parameter may also be other parameters that can reflect different reflection or transmission characteristics of the subcutaneous tissue and the deep fascia layer to the ultrasonic detection waves, which is not specifically limited by this embodiment here.

In this embodiment, the characteristic parameter threshold of the subcutaneous tissue includes a first threshold, which is used to indicate the reflection or transmission characteristic of the subcutaneous tissue, and may be set by a skilled person according to a large number of experimental results and experiences, which is not specifically limited by this embodiment here.

Since the subcutaneous tissue and the deep fascia layer have the different reflection or transmission characteristics to the ultrasonic detection waves, the ultrasonic echo signals meeting the characteristic parameter threshold of the subcutaneous tissue and the ultrasonic echo signals not meeting the characteristic parameter threshold of the subcutaneous tissue may be separated according to the ultrasonic parameter values of the ultrasonic echo signals of the ultrasonic detection waves, so that the ultrasonic echo signals of the subcutaneous tissue can be obtained and the moment the ultrasonic echo signals from the boundary of the subcutaneous tissue are received can be further determined. The distance from the surface of the ultrasonic detector to the boundary of the subcutaneous tissue is the thickness of the subcutaneous tissue.

In this embodiment, the determining, according to ultrasonic parameter values of the ultrasonic echo signals and a characteristic parameter threshold of the subcutaneous tissue, the moment the ultrasonic echo signals from the boundary of the subcutaneous tissue are received may specifically be implemented by adopting the following steps:

Step 1: After the ultrasonic detection waves are emitted, a first mean of ultrasonic parameter values of N consecutive ultrasonic echo signals starting from the first ultrasonic echo signal received are calculated.

If the first mean is less than or equal to the first threshold value, Step 2 is repeated until a first mean of ultrasonic parameter values of a group of N consecutive ultrasonic echo signals acquired is greater than the first threshold value. If the first mean is greater than the first threshold value, Step 3 is executed.

Step 2: A next group of N consecutive ultrasonic echo signals are acquired, and a first mean of ultrasonic parameter values of the group of N consecutive ultrasonic echo signals is calculated.

Step 3: If the first mean is greater than the first threshold value, the N ultrasonic echo signals are taken as a first group of signals, and a second mean of ultrasonic parameter values of N consecutive ultrasonic echo signals following the first group of signals is calculated.

If the second mean is greater than or equal to a second threshold value, Step 2 is executed to acquire a next group of N consecutive ultrasonic echo signals.

Step 4: If the second mean is less than the second threshold value, the moment the last ultrasonic echo signal in the first group of signals is received is determined as a first moment of reception, and the moment a first ultrasonic echo signal following the first group of signals is received is determined as a second moment of reception; and an intermediate moment between the first moment of reception and the second moment of reception is determined as the moment the ultrasonic echo signals from the boundary of the subcutaneous tissue are received.

N is a positive integer, and the value of N may be set by a skilled person according to a large number of experimental results and experiences. For example, the value of N may be set within an interval [1,20], which is not specifically limited by this embodiment here.

For example, N may be 5. If a mean of scattering peaks of ultrasonic echo signals received over a period of five consecutive moments is greater than the first threshold and a mean of scattering peaks of ultrasonic echo signals received over a period of five consecutive moments following the five moments is less than the second threshold, an intermediate moment between the last moment in the former group of five consecutive moments and the first moment in the latter group of five consecutive moments is taken as the moment the ultrasonic echo signals from the boundary of the subcutaneous tissue are received, so that the boundary of the subcutaneous tissue can be determined, and the distance from the skin surface where the ultrasonic detector is located to the boundary of the subcutaneous tissue is the thickness of the subcutaneous tissue.

In addition, the first threshold and the second threshold may be set by a skilled person according to a large number of experimental results and experiences, which is not specifically limited by this embodiment here.

S203: calculating a thickness of the subcutaneous tissue according to the moment the ultrasonic echo signals from the boundary of the subcutaneous tissue are received;

In this embodiment, this step may be specifically implemented in the following way:

A propagation duration of the ultrasonic echo signals from the boundary of the subcutaneous tissue is determined according to the moment of emitting the ultrasonic detection waves and the moment the ultrasonic echo signals from the boundary of the subcutaneous tissue are received; and the thickness of the subcutaneous tissue is calculated according to the propagation duration of the ultrasonic echo signals from the boundary of the subcutaneous tissue and the propagation speed of the ultrasonic echo signals in the subcutaneous tissue.

S204: adding the calculated thickness of the subcutaneous tissue to the length of a measurement blind area of the ultrasonic detector to correct the calculated thickness of the subcutaneous tissue;

Because the ultrasonic detector has a certain measurement blind area when performing measurement, errors will be brought to the measurement of the thickness of the subcutaneous tissue. In this embodiment, the calculated thickness of the subcutaneous tissue may be corrected according to the length of the measurement blind area of the ultrasonic detector.

Specifically, a sum of the thickness of the subcutaneous tissue and the length of the measurement blind area of the ultrasonic detector is calculated according to the currently obtained thickness of the subcutaneous tissue, and the sum of the thickness of the subcutaneous tissue and the length of the measurement blind area of the ultrasonic detector is taken as a corrected thickness value of the subcutaneous tissue.

S205: subtracting the length of a matching layer of the ultrasonic detector from the calculated thickness of the subcutaneous tissue to correct the calculated thickness of the subcutaneous tissue;

The ultrasonic detector includes a piezoelectric layer in which a piezoelectric material vibrates to perform conversion between electrical signals and acoustic signals. The matching layer reduces an acoustic impedance difference between the piezoelectric layer and the object so as to transmit ultrasonic waves generated from the piezoelectric layer to the object to the maximum.

Errors will be brought to the measurement of the thickness of the subcutaneous tissue due to the matching layer of the ultrasonic detector. In this embodiment, the calculated thickness of the subcutaneous tissue may be corrected according to the length of the matching layer of the ultrasonic detector.

Specifically, according to the currently obtained thickness of the subcutaneous tissue, a difference obtained by subtracting the length of the matching layer of the ultrasonic detector from the thickness of the subcutaneous tissue is calculated and taken as a corrected thickness value of the subcutaneous tissue.

S206: adding the calculated thickness of the subcutaneous tissue to a pressing depth of the ultrasonic detector on the skin surface to correct the calculated thickness of the subcutaneous tissue.

When the ultrasonic detector is used to perform measurement, the ultrasonic detector presses the skin surface, and as a result, the skin is sunk inwards by a certain depth (i.e., the pressing depth) under the action of pressure, brining errors to the measurement of the thickness of the subcutaneous tissue. In this embodiment, the calculated thickness of the subcutaneous tissue may be corrected according to the pressing depth of the ultrasonic detector on the skin surface.

Specifically, the adding the calculated thickness of the subcutaneous tissue to a pressing depth of the ultrasonic detector to correct the calculated thickness of the subcutaneous tissue may be specifically implemented in the following way:

A pressing depth of the ultrasonic detector on the skin surface is acquired; a sum of the thickness of the subcutaneous tissue and the pressing depth is calculated and taken as a corrected thickness of the subcutaneous tissue.

Further, the pressing depth of the ultrasonic detector on the skin surface may be acquired in the following way:

The pressing depth of the ultrasonic detector on the skin surface may be determined through measurement information of a sensor, such as a pressure sensor, a displacement sensor, or a position sensor; or, according to data collected during the period from the time when the ultrasonic detector is placed on the skin surface until the pressing is stabilized, an accumulated deformation degree of the tissue is calculated using a block matching method (such as cross correlation or autocorrelation), a filtering method or the like, obtaining the pressing depth.

In addition, in this embodiment, the method for acquiring the pressing depth of the ultrasonic detector on the skin surface may also be implemented by using any method for determining a pressing depth of an ultrasonic detector in the process of measurement in the prior art, which is not specifically limited by this embodiment here.

After the thickness of the subcutaneous tissue is calculated, the calculated thickness of the subcutaneous tissue is corrected according to to-be-corrected contents of the ultrasonic detector. For example, the ultrasonic detector may be an ultrasonic probe, in which case a measurement blind area formed by the morphology of the ultrasonic probe, a matching layer of the ultrasonic probe, etc. should be taken into consideration.

In this embodiment, the calculated thickness value of the subcutaneous tissue may also be corrected according to one or more correction value among a measurement blind area length and matching layer length of the ultrasonic detector and the pressing depth of the ultrasonic detector on the skin surface during measurement, so as to increase the accuracy of the finally measured thickness of the subcutaneous tissue. In addition, besides the measurement blind area length and matching layer length of the ultrasonic detector and the pressing depth of the ultrasonic detector on the skin surface during measurement, the thickness of the subcutaneous tissue may also be corrected according to other factors affecting the measurement of the thickness of the subcutaneous tissue, which is not specifically limited by this embodiment here.

It should be noted that when at least two correction values among the measurement blind area length, the matching layer length and the pressing depth of the ultrasonic detector on the skin surface during measurement are adopted to correct the calculated thickness of the subcutaneous tissue, correction can be performed once according to the at least two correction values; or, as shown in S204 to S206 above, the calculated thickness of the subcutaneous tissue is corrected multiple times according to different correction values, and in this case, since the correction using each correction value is independent, the order of correction based on each correction value is not limited. S204 to S206 above in this embodiment are only illustrative, and in other embodiments, correction may be performed in other ways, which is not specifically limited by this embodiment here. According to the embodiment of the present invention, after ultrasonic detection waves are emitted, a first mean of ultrasonic parameter values of N consecutive ultrasonic echo signals starting from the first ultrasonic echo signal received is calculated, with N being a positive integer; if the first mean is greater than a first threshold value, the N ultrasonic echo signals are taken as a first group of signals, and a second mean of ultrasonic parameter values of N consecutive ultrasonic echo signals following the first group of signals are calculated; if the second mean is less than a second threshold value, a first moment of reception of the last ultrasonic echo signal in the first group of signals and a second moment of reception of a first ultrasonic echo signal following the first group of signals are determined; and an intermediate moment between the first moment of reception and the second moment of reception is determined as the moment the ultrasonic echo signals from the boundary of the subcutaneous tissue are received. Thus, the moment the ultrasonic echo signals from the boundary of the subcutaneous tissue are received can be accurately determined, laying a foundation for the obtainment of the accurate thickness of the subcutaneous tissue. In addition, the obtained thickness of the subcutaneous tissue can be corrected according to the measurement blind area length and matching layer length of the ultrasonic detector and the pressing depth of the ultrasonic detector on the skin surface during measurement, increasing the accuracy of the measurement of the thickness of the subcutaneous tissue.

Embodiment 3

Figure 3:
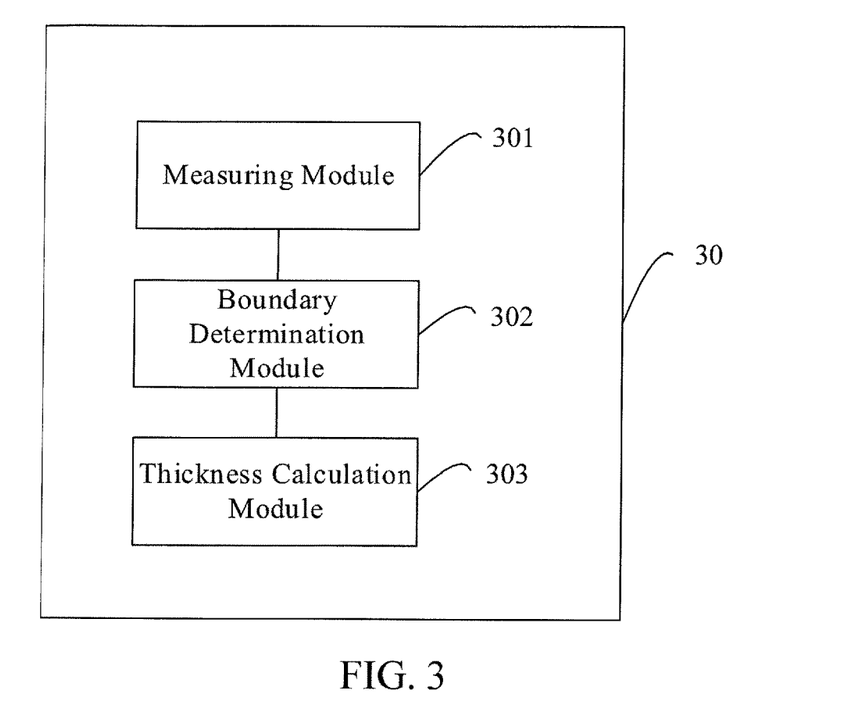
FIG. 3 is a schematic structural diagram of an apparatus for measuring a thickness of a subcutaneous tissue according to Embodiment 3 of the present invention.

FIG. 3 is a schematic structural diagram of an apparatus for measuring a thickness of a subcutaneous tissue according to Embodiment 3 of the present invention. The apparatus for measuring a thickness of a subcutaneous tissue provided by the embodiment of the present invention can execute the processing flows provided by the method embodiments for measuring a thickness of a subcutaneous tissue. As shown in FIG. 3, the apparatus 30 for measuring a thickness of a subcutaneous tissue includes: a measuring module 301, a boundary determination module 302, and a thickness calculation module 303.

Specifically, the measuring module 301 is configured for emitting ultrasonic detection waves inwards from a skin surface and acquiring ultrasonic echo signals of the ultrasonic detection waves.

The boundary determination module 302 is configured for determining, according to ultrasonic parameter values of the ultrasonic echo signals and a characteristic parameter threshold of a subcutaneous tissue, the moment the ultrasonic echo signals from the boundary of the subcutaneous tissue are received.

The thickness calculation module 303 is configured for calculating a thickness of the subcutaneous tissue according to the moment the ultrasonic echo signals from the boundary of the subcutaneous tissue are received.

The apparatus provided by the embodiment of the present invention can be specifically used to execute the method embodiment provided by Embodiment 1 described above, and specific functions will not be described here again.

According to the embodiment of the present invention, ultrasonic detection waves are emitted inwards from a skin surface by an ultrasonic detector, and ultrasonic echo signals of the ultrasonic detection waves are received; the moment the ultrasonic echo signals from the boundary of a subcutaneous tissue are received is determined according to ultrasonic parameter values of the ultrasonic echo signals and a characteristic parameter threshold of the subcutaneous tissue; a thickness of the subcutaneous tissue is calculated according to the moment the ultrasonic echo signals from the boundary of the subcutaneous tissue are received, and thereby the thickness of the subcutaneous tissue can be accurately measured.

Embodiment 4

On the basis of Embodiment 3 above, in this embodiment, the ultrasonic parameter is any of: scattering peak, scatterer density, scatterer distribution characteristic, reflectance value and reflectance value distribution.

Optionally, the boundary determination module is further configured for:

calculating a first mean of ultrasonic parameter values of N consecutive ultrasonic echo signals starting from the first ultrasonic echo signal received after the ultrasonic detection waves are emitted, with N being a positive integer; if the first mean is greater than a first threshold value, taking the N ultrasonic echo signals as a first group of signals, and calculating a second mean of ultrasonic parameter values of N consecutive ultrasonic echo signals following the first group of signals; if the second mean is less than a second threshold value, determining the moment the last ultrasonic echo signal in the first group of signals is received as a first moment of reception and the moment a first ultrasonic echo signal following the first group of signals is received as a second moment of reception; and determining an intermediate moment between the first moment of reception and the second moment of reception as the moment the ultrasonic echo signals from the boundary of the subcutaneous tissue are received.

Optionally, the thickness calculation module is further configured for:

determining a propagation duration of the ultrasonic echo signals from the boundary of the subcutaneous tissue according to the moment of emitting the ultrasonic detection waves and the moment the ultrasonic echo signals from the boundary of the subcutaneous tissue are received; and calculating the thickness of the subcutaneous tissue according to the propagation duration of the ultrasonic echo signals from the boundary of the subcutaneous tissue and the propagation speed of the ultrasonic echo signals in the subcutaneous tissue.

Optionally, the thickness calculation module is further configured for:

adding the calculated thickness of the subcutaneous tissue to the length of a measurement blind area of the ultrasonic detector to correct the calculated thickness of the subcutaneous tissue.

Optionally, the thickness calculation module is further configured for:

subtracting the length of a matching layer of the ultrasonic detector from the calculated thickness of the subcutaneous tissue to correct the calculated thickness of the subcutaneous tissue.

Optionally, the thickness calculation module is further configured for:

acquiring a pressing depth of the ultrasonic detector on the skin surface; and adding the pressing depth to the calculated thickness of the subcutaneous tissue to correct the calculated thickness of the subcutaneous tissue.

The apparatus provided by the embodiment of the present invention can be specifically used to execute the method embodiment provided by Embodiment 2 described above, and specific functions will not be described here again.

According to the embodiment of the present invention, after ultrasonic detection waves are emitted, a first mean of ultrasonic parameter values of N consecutive ultrasonic echo signals starting from the first ultrasonic echo signal received is calculated, with N being a positive integer; if the first mean is greater than a first threshold value, the N ultrasonic echo signals are taken as a first group of signals, and a second mean of ultrasonic parameter values of N consecutive ultrasonic echo signals following the first group of signals is calculated; if the second mean is less than a second threshold value, the moment the last ultrasonic echo signal in the first group of signals is received is determined as a first moment of reception, and the moment a first ultrasonic echo signal following the first group of signals is received is determined as a second moment of reception; and an intermediate moment between the first moment of reception and the second moment of reception is determined as the moment the ultrasonic echo signals from the boundary of the subcutaneous tissue are received. Thus, the moment the ultrasonic echo signals from the boundary of the subcutaneous tissue are received can be accurately determined, laying a foundation for the obtainment of the accurate thickness of the subcutaneous tissue. In addition, the obtained thickness of the subcutaneous tissue can be corrected according to the measurement blind area length and matching layer length of the ultrasonic detector and the pressing depth of the ultrasonic detector on the skin surface during measurement, increasing the accuracy of the measurement of the thickness of the subcutaneous tissue.

Embodiment 5

Figure 4:
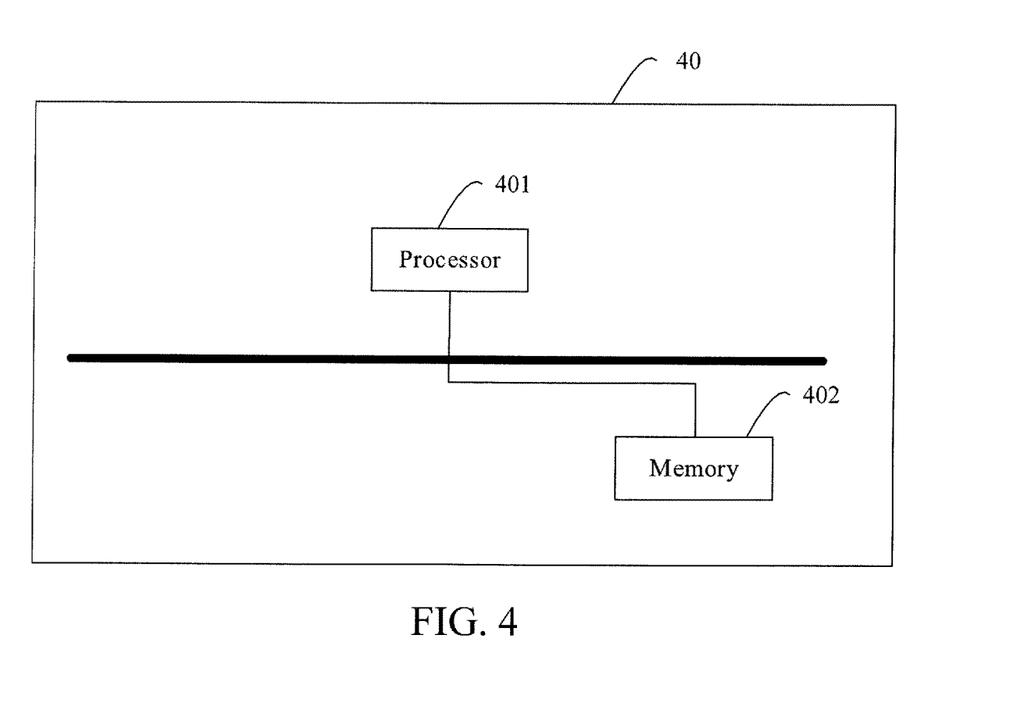
FIG. 4 is a schematic structural diagram of a device for measuring a thickness of a subcutaneous tissue according to Embodiment 5 of the present invention.

FIG. 4 is a schematic structural diagram of a device for measuring a thickness of a subcutaneous tissue according to Embodiment 5 of the present invention. As shown in FIG. 4, the device 40 for measuring a thickness of a subcutaneous tissue includes: a processor 401, a memory 402, and a computer program stored in the memory 402 and executable by the processor 401.

The processor 401 implements the method for measuring subcutaneous tissue thickness provided by any of the method embodiments described above when executing the computer program stored in the memory 402.

According to the embodiment of the present invention, ultrasonic detection waves are emitted inwards from a skin surface by an ultrasonic detector, and ultrasonic echo signals of the ultrasonic detection waves are received; the moment the ultrasonic echo signals from the boundary of a subcutaneous tissue are received is determined according to ultrasonic parameter values of the ultrasonic echo signals and a characteristic parameter threshold of the subcutaneous tissue; a thickness of the subcutaneous tissue is calculated according to the moment the ultrasonic echo signals from the boundary of the subcutaneous tissue are received, and thereby the thickness of the subcutaneous tissue can be accurately measured.

In addition, an embodiment of the present invention further provides a computer-readable storage medium having a computer program stored therein, wherein the computer program implements the method for measuring a thickness of a subcutaneous tissue provided by any of the method embodiments described above when executed by a processor.

In the several embodiments provided by the present invention, it should be understood that the disclosed apparatus and method may be implemented in other ways. For example, the above-described apparatus embodiments are merely illustrative, and for example, the division of the units is only a logical function division. Other division methods may be implemented in practice, for example, a plurality of units or components may be combined or integrated into another system, or some features may be omitted, or not executed. In addition, mutual coupling or direct coupling or communication connection shown or discussed may be indirect coupling or communication connection through some interfaces, apparatuses or units, or may be in electrical, mechanical or other forms.

The units described as separate parts may or may not be physically separated, and parts shown as units may or may not be physical units, that is, they may be located at one position or distributed on a plurality of network units. Some or all of the units can be selected according to actual needs to achieve the purpose of the solution of the embodiment.

In addition, functional units in the embodiments of the present invention may be integrated into one processing unit, or each unit may exist alone physically, or two or more units may be integrated into one unit. The aforementioned integrated unit may be implemented in the form of hardware or in the form of hardware plus a functional software unit.

The aforementioned integrated unit implemented in the form of the functional software unit may be stored in a computer-readable storage medium. The aforementioned functional software unit is stored in a storage medium and includes several instructions for causing a computer device (e.g., a personal computer, a server or a network device) or a processor to execute some steps of the method according to each embodiment of the present invention. The aforementioned storage medium includes: a USB flash disk, a mobile hard disk, a read-only memory (ROM), a random access memory (RAM), a magnetic disk, an optical disk, or other various media capable of storing program codes.

It is clear to those skilled in the art that for convenience and simplicity of description, the aforementioned division of the functional modules is merely used as an example, and in practical applications, the aforementioned functions may be performed by different functional modules as needed, that is, the internal structure of the apparatus is divided into different functional modules to perform all or part of the above-described functions. For the specific operating process of the apparatus described above, refer to the corresponding processes in the aforementioned method embodiments, which will not be described here again.

Those skilled in the art will easily think of other embodiments of the present invention after considering the specification and practicing the invention disclosed herein. The present invention is intended to cover any variation, use or adaptation of the present invention, which follows the general principle of the present invention and includes the common knowledge or conventional technical means in the art which the present invention has not disclosed. The specification and the embodiments are to be regarded as exemplary only, and the true scope and spirit of the present invention is indicated by the following claims.

It should be understood that the present invention is not limited to the precise structure described above and shown in the drawings, and various modifications and changes can be made without departing from its scope. The scope of the present invention is limited only by the appended claims.

The invention claimed is:

1. A method for measuring a thickness of a subcutaneous tissue, comprising:
    emitting ultrasonic detection waves inwards from a skin surface, and acquiring ultrasonic echo signals of the ultrasonic detection waves;
    determining, according to ultrasonic parameter values of the ultrasonic echo signals and a characteristic parameter threshold of a subcutaneous tissue, the moment the ultrasonic echo signals from the boundary of the subcutaneous tissue are received; and
    calculating a thickness of the subcutaneous tissue according to the moment the ultrasonic echo signals from the boundary of the subcutaneous tissue are received,
    wherein determining, according to ultrasonic parameter values of the ultrasonic echo signals and a characteristic parameter threshold of a subcutaneous tissue, the moment the ultrasonic echo signals from the boundary of the subcutaneous tissue are received, comprises:
    calculating a first mean of ultrasonic parameter values of N consecutive ultrasonic echo signals starting from the first ultrasonic echo signal received after the ultrasonic detection waves are emitted, wherein N is a positive integer;
    if the first mean is greater than a first threshold value, taking the N ultrasonic echo signals as a first group of signals, and calculating a second mean of ultrasonic parameter values of N consecutive ultrasonic echo signals following the first group of signals;
    if the second mean is less than a second threshold value, determining the moment the last ultrasonic echo signal in the first group of signals is received as a first moment of reception and the moment a first ultrasonic echo signal following the first group of signals is received as a second moment of reception; and
    determining an intermediate moment between the first moment of reception and the second moment of reception as the moment the ultrasonic echo signals from the boundary of the subcutaneous tissue are received.

2. The method of claim 1, wherein the ultrasonic parameter includes at least one of:
    scattering peak, scatterer density, scatterer distribution characteristic, reflectance value and reflectance value distribution.

3. The method of claim 1, wherein calculating a thickness of the subcutaneous tissue according to the moment the ultrasonic echo signals from the boundary of the subcutaneous tissue are received comprises:
  determining a propagation duration of the ultrasonic echo signals from the boundary of the subcutaneous tissue according to the moment of emitting the ultrasonic detection waves and the moment the ultrasonic echo signals from the boundary of the subcutaneous tissue are received; and
  calculating the thickness of the subcutaneous tissue according to the propagation duration of the ultrasonic echo signals from the boundary of the subcutaneous tissue and the propagation speed of the ultrasonic echo signals in the subcutaneous tissue.

4. The method of claim 1, further comprising, after calculating a thickness of the subcutaneous tissue according to the moment the ultrasonic echo signals from the boundary of the subcutaneous tissue are received:
  adding the calculated thickness of the subcutaneous tissue to the length of a measurement blind area of an ultrasonic detector to correct the calculated thickness of the subcutaneous tissue.

5. The method of claim 1, further comprising, after calculating a thickness of the subcutaneous tissue according to the moment the ultrasonic echo signals from the boundary of the subcutaneous tissue are received:
  subtracting the length of a matching layer of an ultrasonic detector from the calculated thickness of the subcutaneous tissue to correct the calculated thickness of the subcutaneous tissue.

6. The method of claim 1, further comprising, after calculating a thickness of the subcutaneous tissue according to the moment the ultrasonic echo signals from the boundary of the subcutaneous tissue are received:
  acquiring a pressing depth of an ultrasonic detector on the skin surface; and
  adding the pressing depth to the calculated thickness of the subcutaneous tissue to correct the calculated thickness of the subcutaneous tissue.

7. A non-transitory computer-readable storage medium having a computer program stored therein, wherein
  the computer program implements the method of claim 1 when executed by a processor.

8. An apparatus for measuring a thickness of a subcutaneous tissue, comprising:
  a measuring module, configured for emitting ultrasonic detection waves inwards from a skin surface and acquiring ultrasonic echo signals of the ultrasonic detection waves;
  a boundary determination module, configured for determining, according to ultrasonic parameter values of the ultrasonic echo signals and a characteristic parameter threshold of a subcutaneous tissue, the moment the ultrasonic echo signals from the boundary of the subcutaneous tissue are received; and
  a thickness calculation module, configured for calculating a thickness of the subcutaneous tissue according to the moment the ultrasonic echo signals from the boundary of the subcutaneous tissue are received,
  wherein the boundary determination module is further configured for:
  calculating a first mean of ultrasonic parameter values of N consecutive ultrasonic echo signals starting from the first ultrasonic echo signal received after the ultrasonic detection waves are emitted, wherein N is a positive integer;
  if the first mean is greater than a first threshold value, taking the N ultrasonic echo signals as a first group of signals, and calculating a second mean of ultrasonic parameter values of N consecutive ultrasonic echo signals following the first group of signals;
  if the second mean is less than a second threshold value, determining the moment the last ultrasonic echo signal in the first group of signals is received as a first moment of reception and the moment a first ultrasonic echo signal following the first group of signals is received as a second moment of reception; and
  determining an intermediate moment between the first moment of reception and the second moment of reception as the moment the ultrasonic echo signals from the boundary of the subcutaneous tissue are received.

9. The apparatus of claim 8, wherein the ultrasonic parameter includes at least one of:
  scattering peak, scatterer density, scatterer distribution characteristic, reflectance value and reflectance value distribution.

10. The apparatus of claim 8, wherein the thickness calculation module is further configured for:
  determining a propagation duration of the ultrasonic echo signals from the boundary of the subcutaneous tissue according to the moment of emitting the ultrasonic detection waves and the moment the ultrasonic echo signals from the boundary of the subcutaneous tissue are received; and
  calculating the thickness of the subcutaneous tissue according to the propagation duration of the ultrasonic echo signals from the boundary of the subcutaneous tissue and the propagation speed of the ultrasonic echo signals in the subcutaneous tissue.

11. The apparatus of claim 8, wherein the thickness calculation module is further configured for:
  adding the calculated thickness of the subcutaneous tissue to the length of a measurement blind area of an ultrasonic detector to correct the calculated thickness of the subcutaneous tissue.

12. The apparatus of claim 8, wherein the thickness calculation module is further configured for:
  subtracting the length of a matching layer of an ultrasonic detector from the calculated thickness of the subcutaneous tissue to correct the calculated thickness of the subcutaneous tissue.

13. The apparatus of claim 8, wherein the thickness calculation module is further configured for:
  acquiring a pressing depth of an ultrasonic detector on the skin surface; and
  adding the pressing depth to the calculated thickness of the subcutaneous tissue to correct the calculated thickness of the subcutaneous tissue.

* * * * *